(12) United States Patent
Wallnewitz et al.

(10) Patent No.: US 9,731,091 B2
(45) Date of Patent: Aug. 15, 2017

(54) ELBOW FOR A RESPIRATION MASK (71) Applicant: Dräger Medical GmbH, Lübeck (DE)

(72) Inventors: Oliver Wallnewitz, Lübeck (DE);
Krisztina Soltész, Lübeck (DE);
Alexandra Gawrysch, Bremerhaven (DE)

(73) Assignee: Draegerwerk AG & Co. KGaA, Lübeck (DE)

( * ) Notice: Subject to any disclaimer, the term of this patent is extended or adjusted under 35 U.S.C. 154(b) by 636 days.

(21) Appl. No.: 14/063,009

(22) Filed: Oct. 25, 2013

(65) Prior Publication Data
US 2014/0116432 A1 May 1, 2014

(30) Foreign Application Priority Data
Oct. 25, 2012 (DE) .................... 10 2012 020 917

(51) Int. Cl.
*A62B 9/04* (2006.01)
*A61M 16/08* (2006.01)
(Continued)

(52) U.S. Cl.
CPC .... *A61M 16/0816* (2013.01); *A61M 16/0057* (2013.01); *A61M 16/06* (2013.01);
(Continued)

(58) Field of Classification Search
CPC .. A61M 16/00; A61M 16/0816; A61M 16/20; A61M 16/0057; A61M 16/06; A61M 16/0875; A61M 16/003; A61M 16/009; A61M 16/08; A61M 16/208; A61M 16/209; A62B 7/00; A62B 9/00; A62B 18/00;
(Continued)

(56) References Cited

U.S. PATENT DOCUMENTS 1,336,123 A * 4/1920 Barnes .................... F16L 29/00
251/149
2,845,282 A * 7/1958 Mueller ................ F16L 27/093
285/137.11
(Continued)

FOREIGN PATENT DOCUMENTS

AU   WO 2007143792 A1 * 12/2007  ............ A61M 16/06
CN   1886167 A   12/2006
(Continued)

*Primary Examiner* — Bradley Philips
*Assistant Examiner* — Victoria Leszczak
(74) *Attorney, Agent, or Firm* — McGlew and Tuttle, P.C.

(57) ABSTRACT

An elbow (1), for a respiration mask for the artificial respiration of a patient, includes an angular tube (30), which defines a breathing gas duct (10), with a tube port (11) with an inlet opening (12) for connecting a breathing tube (7) and with a mask port (13) with an outlet opening (14) for connecting the respiration mask (9). The elbow also includes an anti-suffocation valve (18) and carbon dioxide expiration openings (19). The elbow (1) is able to be switched, while being able to be handled in a simple manner, in different open and closed states for the anti-suffocation valve (18) and the carbon dioxide expiration openings (19). The elbow (1) includes only one (a single) switching member (20) for activating and deactivating the anti-suffocation valve (18) and the carbon dioxide expiration openings (19).

20 Claims, 4 Drawing Sheets (51) Int. Cl.
*A61M 16/06* (2006.01)
*A61M 16/20* (2006.01)
*A61M 16/00* (2006.01)

(52) U.S. Cl.
CPC .......... *A61M 16/20* (2013.01); *A61M 16/208* (2013.01); *A61M 16/0875* (2013.01); *A61M 16/201* (2014.02)

(58) Field of Classification Search
CPC . A62B 9/04; A62B 18/20; F16L 27/00–39/00
USPC ...................................................... 128/201.1
See application file for complete search history.

(56) References Cited

U.S. PATENT DOCUMENTS

| | | | | |
|---|---|---|---|---|
| 3,476,141 A * | 11/1969 | Tillman | .................. | F16K 31/36 137/498 |
| 3,786,837 A * | 1/1974 | Pipkins | .................. | B67D 7/002 137/625.3 |
| 4,064,875 A | 12/1977 | Cramer et al. | | |
| 4,295,633 A * | 10/1981 | Sigmon | .................. | F16D 65/14 188/366 |
| 4,506,665 A * | 3/1985 | Andrews | ............... | A61M 16/08 128/202.27 |
| 5,083,588 A * | 1/1992 | Truchet | .................. | F16L 29/04 137/614.02 |
| 5,438,981 A * | 8/1995 | Starr | ....................... | A62B 7/12 128/205.24 |
| 5,560,354 A * | 10/1996 | Berthon-Jones | ...... | A61M 16/06 128/204.18 |
| 5,647,355 A * | 7/1997 | Starr | ....................... | A62B 7/12 128/205.24 |
| 5,878,743 A * | 3/1999 | Zdrojkowski | ............ | A62B 9/02 128/204.23 |
| 5,896,857 A * | 4/1999 | Hely | ........................ | A62B 9/02 128/203.11 |
| 5,937,851 A * | 8/1999 | Serowski | ............... | A61M 16/06 128/202.27 |
| 6,119,723 A | 9/2000 | Kenyon | | |
| 6,478,026 B1 * | 11/2002 | Wood | ................ | A61M 16/0666 128/207.13 |
| 6,584,977 B1 * | 7/2003 | Serowski | ............... | A61M 16/06 128/206.24 |
| 6,615,831 B1 * | 9/2003 | Tuitt | ...................... | A61M 16/08 128/204.18 |
| 6,851,425 B2 * | 2/2005 | Jaffre | .................... | A61M 16/08 128/204.18 |
| 7,059,325 B2 * | 6/2006 | Hollis | ................. | A61M 16/208 128/204.18 |
| 7,370,654 B2 * | 5/2008 | Persson | ............ | A61M 16/0468 128/207.12 |
| 7,559,327 B2 * | 7/2009 | Hernandez | ........... | A61M 16/06 128/203.22 |
| 7,568,482 B2 * | 8/2009 | Jaffre | .................... | A61M 16/08 128/204.18 |
| 7,597,100 B2 * | 10/2009 | Ging | ..................... | A61M 16/06 128/204.18 |
| 7,658,189 B2 * | 2/2010 | Davidson | ............ | A61M 16/06 128/205.25 |
| 7,762,252 B2 * | 7/2010 | Prete | .................... | A62B 18/006 128/204.18 |
| 7,874,292 B2 * | 1/2011 | Smith | .................... | A61M 16/06 128/202.27 |
| 7,909,035 B2 * | 3/2011 | Thornton | ............. | A61M 16/06 128/205.25 |
| 7,942,150 B2 * | 5/2011 | Guney | .................. | A61M 16/06 128/207.13 |
| 8,136,525 B2 * | 3/2012 | Lubke | .................. | A61M 16/06 128/205.25 |
| 8,205,615 B1 * | 6/2012 | Ho | ........................ | A61M 16/06 128/200.24 |
| 8,251,066 B1 * | 8/2012 | Ho | ........................ | A61M 16/06 128/204.18 |
| 8,261,745 B2 * | 9/2012 | Chandran | ............. | A61M 16/06 128/205.25 |
| 8,439,035 B2 * | 5/2013 | Dantanarayana | .... | A61B 5/0876 128/203.11 |
| 8,505,535 B2 * | 8/2013 | Jones | .................... | A61M 16/06 128/204.21 |
| 8,851,075 B2 * | 10/2014 | Ng | .................... | A61M 16/0666 128/206.28 |
| 2002/0078960 A1 * | 6/2002 | Cise | .................. | A61M 16/0463 128/205.24 |
| 2002/0162553 A1 * | 11/2002 | Hamilton | ............... | A61M 16/00 128/204.18 |
| 2003/0005931 A1 * | 1/2003 | Jaffre | .................... | A61M 16/08 128/204.18 |
| 2003/0127096 A1 * | 7/2003 | McAuliffe | ............ | A61M 16/00 128/204.18 |
| 2004/0094157 A1 * | 5/2004 | Dantanarayana | .... | A61B 5/0876 128/206.21 |
| 2004/0112385 A1 * | 6/2004 | Drew | ................. | A61M 16/0638 128/206.21 |
| 2006/0266361 A1 * | 11/2006 | Hernandez | ........... | A61M 16/06 128/206.11 |
| 2006/0283452 A1 * | 12/2006 | Woodard | ............. | A61M 16/06 128/205.25 |
| 2007/0095350 A1 * | 5/2007 | Darkin | .................. | A61M 16/06 128/206.24 |
| 2008/0047561 A1 | 2/2008 | Fu et al. | | |
| 2009/0032026 A1 * | 2/2009 | Price | ..................... | A61M 16/06 128/207.11 |
| 2009/0065729 A1 * | 3/2009 | Worboys | ............... | A61M 16/06 251/367 |
| 2009/0260628 A1 * | 10/2009 | Flynn, Sr. | ......... | A61M 16/0078 128/203.28 |
| 2010/0154799 A1 * | 6/2010 | Brewer | ............. | A61M 16/0833 128/207.14 |
| 2011/0180071 A1 * | 7/2011 | Veliss | .................... | A61M 16/06 128/206.21 |
| 2011/0209709 A1 * | 9/2011 | Davidson | ............... | A61M 16/06 128/205.25 |
| 2011/0285126 A1 * | 11/2011 | Jahan | ..................... | B05B 1/044 285/305 |
| 2012/0055471 A1 * | 3/2012 | Hadas | ................ | A61M 16/0816 128/201.19 |
| 2012/0191037 A1 * | 7/2012 | Patel | ..................... | F16K 5/0407 604/30 |
| 2014/0069428 A1 * | 3/2014 | Sears | ..................... | F16K 5/0407 128/204.21 |
| 2015/0369410 A1 * | 12/2015 | Weiland | ..................... | F16K 1/38 251/149.6 |

FOREIGN PATENT DOCUMENTS

| | | | | |
|---|---|---|---|---|
| CN | 101229410 A | 7/2008 | | |
| CN | 102256646 A | 11/2011 | | |
| WO | 00/38772 A1 | 7/2000 | | |
| WO | 2005/051468 A1 | 6/2005 | | |
| WO | WO 2006122092 A2 * | 11/2006 | .......... | A61B 5/0836 |
| WO | 2012/023107 A1 | 2/2012 | | |
| WO | 2013/040198 A2 | 3/2013 | | |

* cited by examiner

ELBOW FOR A RESPIRATION MASK

CROSS REFERENCE TO RELATED APPLICATIONS

This application claims the benefit of priority under 35 U.S.C. §119 of German Patent Application DE 10 2012 020 917.7 filed Oct. 25, 2012, the entire contents of which are incorporated herein by reference.

FIELD OF THE INVENTION

The present invention pertains to an elbow for a respiration mask for the artificial respiration of a patient, and to a mask system and to a respiration system.

BACKGROUND OF THE INVENTION

Artificial or assisted respiration of patients is necessary for various medical applications. Respirators are used for the artificial respiration of patients. The expiration gas expired by the patient can be used again at least partly as inspiration gas in some respirators, which are used especially in the area of anesthesia, i.e., these respirators are respiration systems with a breathing air circulation system.

Artificial respiration of patients is performed in the clinical area or even in case of respiration at home. For this, the breathing gas is to be fed to the patient through at least one breathing tube, especially the inspiration tube. The inspiration tube and an expiration tube are connected here, in general, to a Y-piece, and this is in turn connected to an elbow. The breathing gas is fed through the elbow to a respiration mask, which lies on the area of the face of the patient. The angular tube defines a breathing gas duct, through which the breathing air can be fed to the patient and the expired air can be removed. A breathing tube or the Y-piece can be connected to a tube port of the elbow and the respiration mask can be connected to a mask port of the elbow. The elbow has an anti-suffocation valve and carbon dioxide expiration openings. The anti-suffocation valve is used to prevent the patient from suffocating, especially in case of a defect of or damage to the respirator. The patient can thus draw breathing air directly from the environment of the elbow. Higher concentrations of carbon dioxide shall be prevented from building up in dead spaces of the elbow with the carbon dioxide expiration openings. It may be necessary for various applications of the elbow to have both the anti-suffocation valve and the carbon dioxide expiration openings opened or activated or to have only the anti-suffocation valve opened and to have the carbon dioxide expiration openings closed or deactivated. A complicated activation and deactivation by means of different switching members at the elbow is disadvantageously necessary for this.

An elbow with an anti-suffocation valve is known from U.S. Pat. No. 5,647,355. The anti-suffocation valve makes possible an automatic connection to the ambient air in case of a defect and has a primary inlet and a secondary inlet as well as an outlet.

SUMMARY OF THE INVENTION

An object of the present in invention is to make available an elbow for a mask system or a respiration system, which can be handled easily and can be switched into different opened and closed states for the anti-suffocation valve and the carbon dioxide expiration openings.

This object is accomplished with an elbow, comprising an angular tube, which defines a breathing gas duct, with a tube port with an inlet opening for connecting a breathing tube or Y-piece and with a mask port with an outlet opening for connecting the respiration mask, an anti-suffocation valve, and carbon dioxide expiration openings, wherein the elbow comprises only one switching member for activating and deactivating the anti-suffocation valve and carbon dioxide expiration openings. The elbow has only one switching member for activating and deactivating both the anti-suffocation valve and the carbon dioxide expiration openings. As a result, the elbow can be actuated in an especially simple manner, because both the anti-suffocation valve and the carbon dioxide expiration openings can be activated and deactivated, i.e., opened and closed, with the only one switching member. The elbow can thus be handled especially simply and comfortably for opening and closing the anti-suffocation valve and the carbon dioxide expiration openings.

In an additional embodiment, the angular tube has a first straight section with an inlet opening, a second straight section with an outlet opening and a tube bend, e.g., with a curvature between 30° and 120°, especially in the range of 90°. The angular tube advantageously has the first and second sections and no bend. The angular tube is thus designed as a straight piece of tube in this embodiment. The bend preferably has a curvature at an angle between 0° and 180°.

The switching member is designed especially as a ring, especially a rotating ring, a lever, a slide or a rotating wheel. A ring, especially a rotating ring, at the elbow can be actuated by the user of the elbow in an especially simple manner; in particular, the ring may be mounted pivotably about an axis of rotation and/or mounted movably in the direction of a longitudinal axis of the elbow for different switching positions of the switching member.

In another embodiment, the elbow comprises a first actuating element for activating and deactivating the anti-suffocation valve at the anti-suffocation valve and a second actuating element for activating and deactivating the carbon dioxide expiration openings at the carbon dioxide expiration openings.

In an additional embodiment, the first and second actuating elements are in functional mechanical connection, especially with a mechanism, with the switching member, so that the first and second actuating elements can be moved by means of the only one switching member between an activation position and a deactivation position, and/or the elbow comprises a mechanism for mechanically connecting the switching member with the first and second actuating elements. The first and second actuating elements are mobile or movable between an activation position and a deactivation position, and this can be performed by means of the only one switching member. Thus, both the first actuating element and the second actuating element can be moved or movable between the activation position and the deactivation position by means of the only one switching member. The mechanism is advantageously necessary for also making it possible to move both the first and second actuating elements between the activation position and the deactivation position by means of the only one switching member. If the switching member is designed, for example, as a rotating wheel, only a rotating motion can be performed with the switching member, and the first and/or second actuating element performs, on the other hand, a translatory motion between the activation position and the deactivation position and vice versa. The mechanism is necessary for this reason to convert the rotary motions of the rotating wheel as a switching member into the translatory motion of the first and/or second actuating element and vice versa.

The first actuating element is preferably designed as a flap, a roller blind or a diaphragm, especially an elastically deformable diaphragm, and/or the switching member is arranged at the elbow on the outside and/or the first and/or second actuating member is arranged at the elbow on the inside, especially within the breathing gas duct. An anti-suffocation opening at the angular tube can be opened and closed by means of a flap or diaphragm in an especially simple manner, so that the flap or diaphragm as a first actuating element is part of the anti-suffocation valve.

A fork part is fastened to the switching member, especially the ring, in one variant, so that the fork part also performs a motion of the switching member and there is no contact between the fork part and the flap or diaphragm in the activation position of the fork part and the fork part is in contact with the flap or diaphragm in the deactivation position of the fork part and an anti-suffocation opening of the anti-suffocation valve is closed because of the contact with the valve or diaphragm. The flap or diaphragm can be moved in a simple manner between the activation position and the deactivation position by means of the fork part or lever part, which is connected especially rigidly to the actuating member.

The second actuating member is preferably formed by the switching member, especially the ring, or the second actuating element is formed by a flap, a roller blind or a diaphragm. The second actuating element may be formed by the switching member itself or by a separate component, e.g., a flap, a roller blind or a diaphragm.

The switching member is mounted movably between at least three different switching positions in another embodiment.

In particular, the anti-suffocation valve and the carbon dioxide expiration openings are activated in a first switching position of the switching member, the anti-suffocation valve is activated and the carbon dioxide expiration openings are deactivated in a second switching position of the switching member, and the anti-suffocation valve is deactivated and the carbon dioxide expiration openings are deactivated in a third switching position of the switching member.

The anti-suffocation valve is deactivated and the carbon dioxide expiration openings are activated in a fourth switching position of the switching member in another embodiment.

In an additional variant, the ring is mounted movably on the outside at a straight section of the angular tube in the direction of a longitudinal axis of the straight section. The ring surrounds on the outside the angular tube, extending completely around especially a straight section of the angular tube, and the ring is preferably made coaxial and/or concentric with a longitudinal axis of the straight section of the angular tube, at which the ring is arranged.

In another variant, the ring is designed as a rotating ring and is rotatable about an axis of rotation, which corresponds to the longitudinal axis of the straight section of the angular tube and/or the ring is connected movably with the angular tube by means of a threaded connection and/or a sliding block guide and/or the mechanism and can especially be fixed detachably in the different switching positions by means of the threaded connection and/or the sliding block guide and/or the mechanism. The ring is additionally rotatable or pivotable about an axis of rotation, so that the ring can be fixed detachably as a result as a rotating ring in the different switching positions based on this rotary or pivoting motion. To move the ring as a rotating ring from the first switching position into the second switching position, the rotating ring is to be rotated, for example, at first about the axis of rotation in order to detach the ring from the first switching position in its fixed position, after which the ring is to be moved as a rotating ring in the direction of the longitudinal axis by a translatory motion, and the ring can be detachably fixed as a rotating ring in the second switching position by means of an additional rotary motion. This analogously applies to further switching positions of the rotating ring.

Mask system according to the present invention with a respiration mask and with an elbow, wherein the elbow is designed as an elbow described in this patent application.

Respiration system according to the present invention, comprising a respirator, at least one breathing tube, an elbow and a respiration mask, wherein the elbow is designed as an elbow described in this patent application.

The angular tube is preferably a one-part or multipart angular tube.

In particular, only one carbon dioxide expiration opening, especially one large carbon dioxide expiration opening, will be considered as carbon dioxide expiration openings.

In another embodiment, the elbow consists at least partly and especially entirely of plastic.

The respirator comprises, in particular, an inspiration tube and an expiration tube and/or the respirator has a Y-piece, and the inspiration tube and the expiration tube are preferably connected to the Y-piece.

In another embodiment, the respirator comprises a feed means for feeding oxygen to the inspiration gas.

In an additional embodiment, the respirator comprises a gas delivery means. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
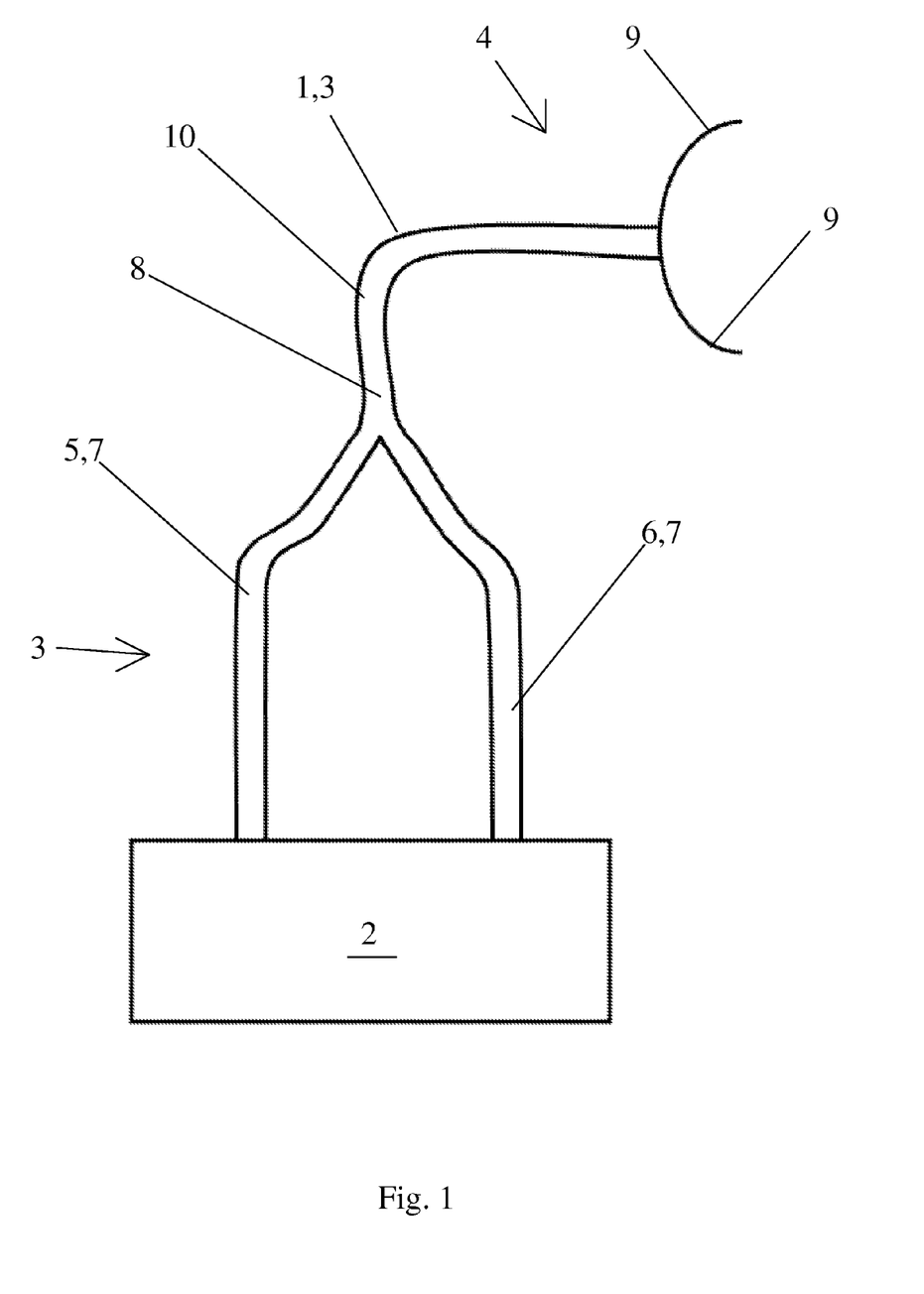
FIG. 1 is a simplified view of a respirator.

Referring to the drawings in particular, FIG. 1 shows a respirator 2. The inspiration gas fed to the patient to be respirated is fed to the patient through an inspiration tube 5 as a breathing tube 6 as part of a breathing air line system. After following through the inspiration tube 5 and a Y-piece 8, the inspiration gas is fed to the patient through an elbow 1 and a respiration mask 9. The air expired by the patient is removed through an expiration tube 6 acting as a breathing tube 7. The respirator 2 forms a respiration system 3 with the breathing tube 7, the Y-piece 8, the elbow 1 and the respiration mask 9. The elbow 1 and the respiration mask 9 form a mask system 4.

The respirator 2 can be connected to the power supply system of a hospital with a power connection cable, not shown, as well as a power plug. In addition, the respirator 2 has gas supply lines (not shown) for connection to a central oxygen and/or air and/or nitrous oxide supply of the hospital.

Figure 2:
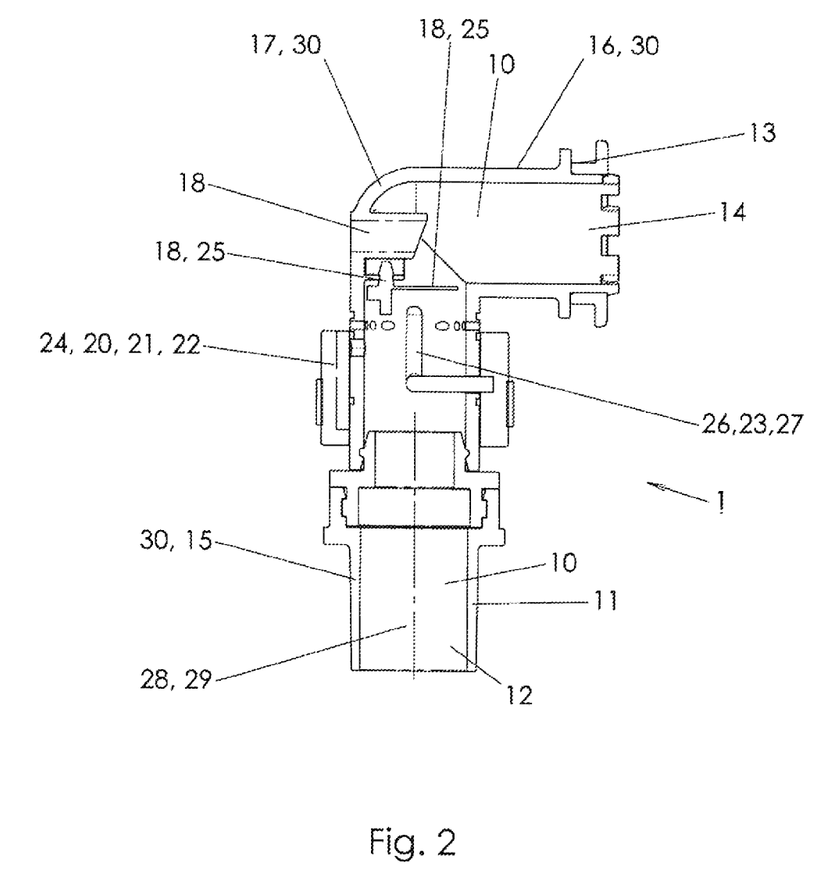
FIG. 2 is a longitudinal sectional view of an elbow with an activated anti-suffocation valve and activated carbon dioxide expiration openings.
Figure 3:
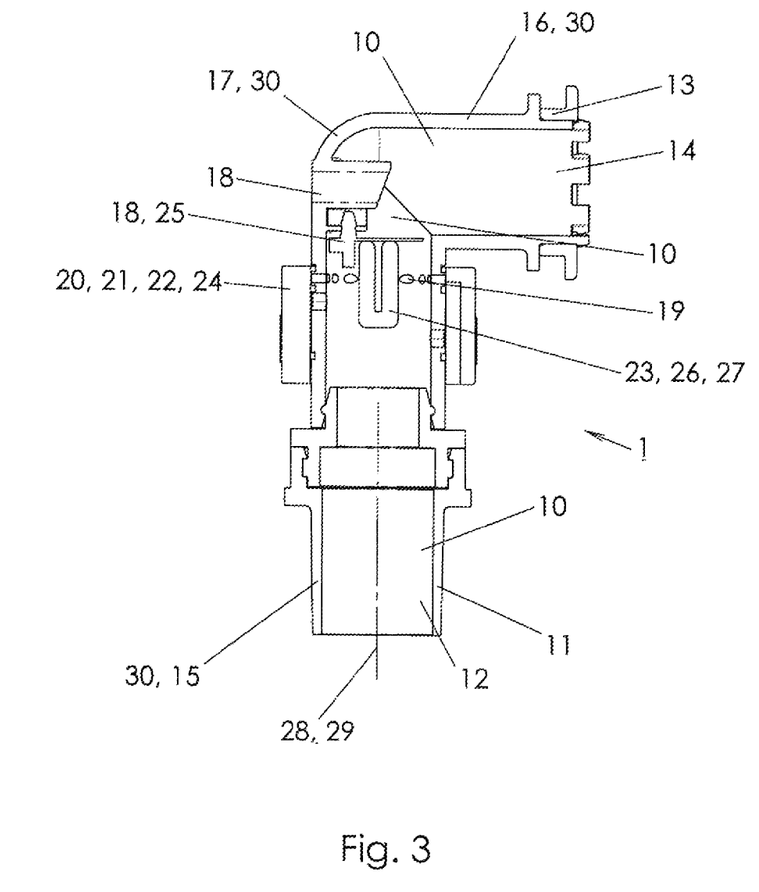
FIG. 3 is a longitudinal sectional view of an elbow with an activated anti-suffocation valve and deactivated carbon dioxide expiration openings.
Figure 4:
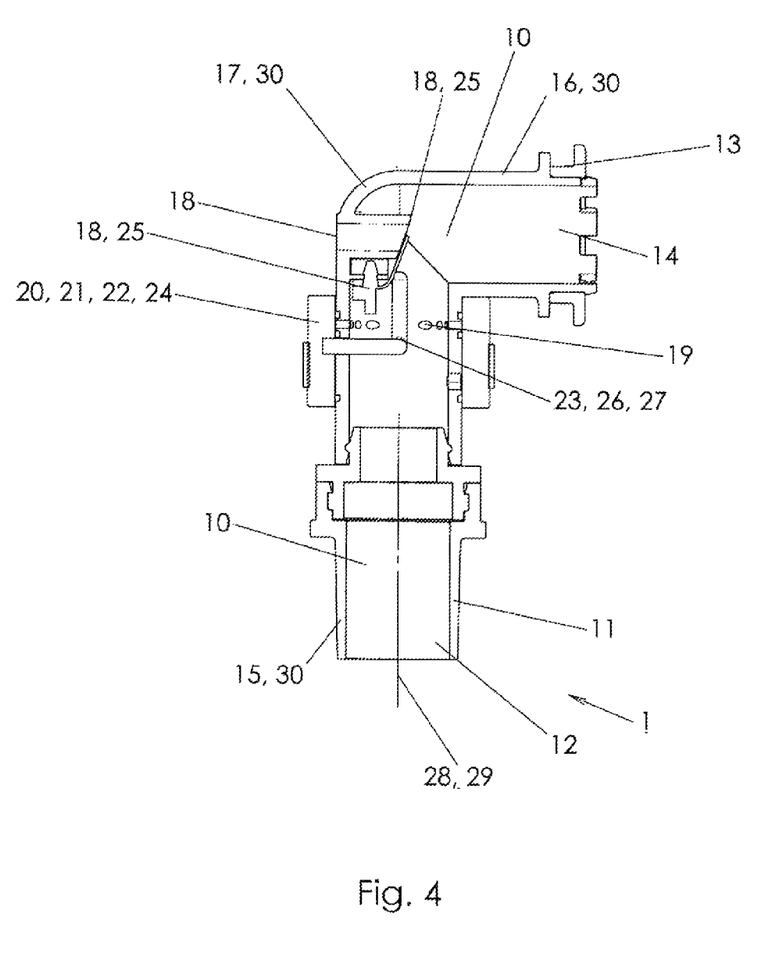
FIG. 4 is a longitudinal sectional view of an elbow with a deactivated anti-suffocation valve and activated carbon dioxide expiration openings.

FIGS. 2 through 4 show a longitudinal view of the elbow 1. The elbow 1 has a multipart angular tube 30 made of thermoplastic plastic, which defines a breathing gas duct 10 for passing through expiration gas and inspiration gas or breathing air. The angular tube 30 comprises a first straight section 15 with an inlet opening 12 for introducing the inspiration gas and a second straight section 16 with an outlet opening 14 for discharging the inspiration gas into the respiration mask 9. The inlet and outlet openings 12, 14 are used, furthermore, in the reversed manner for passing through the expiration gas. A tube port 11 for joining or connection to the Y-piece 8 or to a breathing tube 7 is provided at the first straight section 15. A mask port 13 is analogously provided at the second straight section 16 for connecting or fastening the respiration mask 9. The first and second straight sections 15, 16 are connected to one another by means of a bend 17, which has a curvature of essentially 90°. The first and second sections 15, 16 or a longitudinal axis 28 of the first and second straight sections 15, 16, where only the longitudinal axis 28 of the first section 15 is shown, are at essentially right angles to one another as a result.

The elbow 1 is provided, furthermore, with an anti-suffocation valve 18. The anti-suffocation valve 18 is formed by an anti-suffocation opening indicated by broken lines in FIGS. 2 through 4 as well as a diaphragm 25. The anti-suffocation opening of the anti-suffocation valve 18 can be opened and closed by means of diaphragm 25. With the anti-suffocation valve 18 opened or with an anti-suffocation opening opened, the anti-suffocation valve is activated, and, conversely, the anti-suffocation valve 18 is deactivated in case of an anti-suffocation opening closed by diaphragm 25. The anti-suffocation valve 18 is used to continue to make respiration of the patient with air from the environment possible in case of damage or failure at the respirator 2. Air can be fed from the environment for respirating the patient to be respirated artificially directly through the elbow 1 by means of the anti-suffocation valve 18.

Carbon dioxide may collect in dead spaces of the elbow 1. The elbow 1 is additionally provided for this reason with carbon dioxide expiration openings (a carbon dioxide opening arrangement of one or more openings) 19. The carbon dioxide can be removed through the carbon dioxide expiration openings 19 into the environment. With carbon dioxide expiration openings 19 activated, these are opened, and they are closed when the carbon dioxide expiration openings 19 are deactivated. The elbow 1 is provided, furthermore, with only one switching member 20 for both activating and deactivating the anti-suffocation valve 18 as well as for activating and deactivating the carbon dioxide expiration openings 19. The switching member 20 is designed as a ring 21, which also represents a rotating ring 22, because the ring 21 is mounted not only movably through a translatory motion in the direction of a longitudinal axis 28 of the first straight section 15, but also pivotably or rotatorily movably about an axis of rotation 29. The axis of rotation 29 of the rotating ring 22 corresponds to the longitudinal axis 28 of the first straight section 15 of the angular tube 30. The rotating ring 22 is formed on the outside at the first straight section 15 of the angular tube 30.

The elbow 1 has, furthermore, a first actuating element 23 for activating and deactivating or for opening and closing the anti-suffocation opening of the anti-suffocation valve 18. The first actuating element 23 is formed by an elastically deformable diaphragm 25. The angular tube 30 has, furthermore, an opening or a slot, through which is led a fork part 26 as a mechanism 27, and said fork park 26 is connected rigidly to the rotating ring 22.

The rotating ring 22 as a switching member 20 can be moved between three switching positions. A first switching position of the switching member 20, in which both the anti-suffocation valve 18 and the carbon dioxide expiration openings 19 are activated, is shown in FIG. 2. The anti-suffocation valve 18 is activated and the carbon dioxide expiration openings 19 are deactivated or closed in a second switching position of the switching member 20, which position is shown in FIG. 3. Both the anti-suffocation valve 18 and the carbon dioxide expiration openings 19 are closed or deactivated in a third switching position of the switching member 20, and this switching position is shown in FIG. 4. In the second and third switching positions of the rotating ring 22, the rotating ring 22 completely closes all carbon dioxide expiration openings 19. The fork part 26 is rigidly connected to the rotating ring 22 and the fork part 26 is in contact with the diaphragm 25 in the second switching position of the switching member 20 because of the translatory motion of the rotating ring 22 in the direction of the longitudinal axis 28. The switching member 20, i.e., the rotating ring 22, also forms a second actuating element 24 for opening and closing the carbon dioxide expiration openings 19. The rotating ring 22 completely closes the carbon dioxide expiration openings 19 formed circumferentially in the second and third switching positions of the switching member 20 shown in FIGS. 3 and 4.

The fork part 26 is rigidly connected to the switching member 20 and the fork part 26 also performs a translatory motion in the direction of the longitudinal axis 28 of the first section 15 during a translatory motion of the switching member 20 between the three switching positions. There is no contact between the fork part 26 and the diaphragm 25 in the first switching position of the switching member 20 according to FIG. 2. There already is a contact between diaphragm 25 and fork part 26 in the second switching position of the switching member 20 shown in FIG. 3, but the diaphragm 25 is still in a position in which the anti-suffocation opening is not closed. The fork part 26 also moves upward according to the view shown in FIGS. 3 and 4 during a further motion of the switching member 20 from the second into the third switching position, so that the diaphragm 25 closes as a result the anti-suffocation opening of the anti-suffocation valve 18.

Ring 21 as a rotating ring 22 is, furthermore, pivotable about the axis of rotation 29. The switching member 20 can be fixed detachably in the three switching positions at the rest of the elbow or the angular tube 30 by means of a sliding block guide, not shown separately, and/or the mechanism 27, which is shown only partially as a fork part 26. This detachable connection is established and this detachable connection is broken (deactivated) between the switching positions by pivoting the rotating ring 22 about the axis of rotation 29.

Considered on the whole, essential advantages are associated with the elbow 1 according to the present invention. Elbow 1 is provided with only one switching member 20 as a rotating ring 22, and both the anti-suffocation valve 18 and the carbon dioxide expiration openings 19 can be activated and deactivated by means of the only one switching member 20. As a result, the elbow 1 can be operated and handled in an especially simple and practical manner. Thus, it is not necessary to actuate separate actuating members for the anti-suffocation valve 18 and the carbon dioxide expiration openings 19, but this can be performed with the only one switching member 20 in a simple and practical manner.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 1 | Elbow |
| 2 | Respirator |
| 3 | Respiration system |
| 4 | Mask system |
| 5 | Inspiration tube |
| 6 | Expiration tube |
| 7 | Breathing tube |
| 8 | Y-piece |
| 9 | Respiration mask |
| 10 | Breathing gas duct |
| 11 | Tube port |
| 12 | Inlet opening |
| 13 | Mask port |
| 14 | Outlet opening |
| 15 | First straight section with inlet opening |
| 16 | Second straight section with outlet opening |
| 17 | Bend |
| 18 | Anti-suffocation valve |
| 19 | Carbon dioxide expiration openings |
| 20 | Switching member |
| 21 | Ring |
| 22 | Rotating ring |
| 23 | First actuating element |
| 24 | Second actuating element |
| 25 | Diaphragm |
| 26 | Fork part |
| 27 | Mechanism |
| 28 | Longitudinal axis |
| 29 | Axis of rotation |
| 30 | Angular tube |

What is claimed is:

1. A patient artificial respiration mask elbow comprising:
an angular tube defining a breathing gas duct;
a tube port with an inlet opening for connecting to a breathing tube or Y-piece;
a mask port with an outlet opening for connecting to a respiration mask;
an anti-suffocation valve with an anti-suffocation opening, said anti-suffocation valve automatically and selectively providing a flow path from said mask port through the anti-suffocation opening to ambient air in case of a defect;
carbon dioxide expiration openings, said carbon dioxide expiration openings being separate and spaced from said anti-suffocation valve and said anti-suffocation opening; and
only one switching member selectively movable for activating and deactivating the anti-suffocation valve and for activating and deactivating the carbon dioxide expiration openings.

2. The elbow in accordance with claim 1, wherein the switching member comprises one of a rotating ring, a lever, a slide and a rotating wheel.

3. The elbow in accordance with claim 1, further comprising a first actuating element for activating and deactivating the anti-suffocation valve at the anti-suffocation valve and a second actuating element for activating and deactivating the carbon dioxide expiration openings at the carbon dioxide expiration openings.

4. The elbow in accordance with claim 3, wherein one of:
the first actuating element and the second actuating element each comprise a mechanical functional connection mechanism with the switching member, the first actuating element and the second actuating element moving between an activation position and a deactivation position by means of the only one switching member; and
the elbow further comprises a mechanism for mechanically connecting the switching member to the first actuating element and to the second actuating element.

5. The elbow in accordance with claim 3 wherein at least one of:
the first actuating element comprises a flap, a roller blind or an elastically deformable diaphragm; and
the switching member is arranged on the outside at the elbow; and
one of the first actuating element and the second actuating element is arranged within the breathing gas duct, at the elbow.

6. The elbow in accordance with claim 5, wherein
a fork part is fastened to the switching member and performs a motion of the switching member with no contact between the fork part and the flap or diaphragm in an activation position of the fork part;
the fork part is in contact with the flap or diaphragm in a deactivation position of the fork part; and
an anti-suffocation opening of the anti-suffocation valve is closed upon contact with the flap or diaphragm.

7. The elbow in accordance with claim 3, wherein at least one of:
the second actuating element is formed as a part of the switching member; and
the second actuating element is formed by a flap, a roller blind or a diaphragm.

8. The elbow in accordance with claim 1, wherein the switching member is mounted movably between at least three different switching positions.

9. The elbow in accordance with claim 8, wherein:
the anti-suffocation valve and the carbon dioxide expiration openings are activated in a first switching position of the at least three different switching positions of the switching member;
the anti-suffocation valve is activated and the carbon dioxide expiration openings are deactivated in a second switching position of the at least three different switching positions of the switching member; and
the anti-suffocation valve is deactivated and the carbon dioxide expiration openings are deactivated in a third switching position of the switching member.

10. The elbow in accordance with claim 9, wherein:
the at least three different switching positions comprises four switching positions; and
the anti-suffocation valve is deactivated and the carbon dioxide expiration openings are activated in a fourth switching position of the switching member.

11. The elbow in accordance with claim 4, wherein the switching member comprises a ring mounted on an outside at a straight section of the angular tube, the ring being movable in a direction of a longitudinal axis of the straight section.

12. The elbow in accordance with claim 11, wherein the ring is at least one of:
a rotating ring that is rotatable about an axis of rotation which corresponds to the longitudinal axis of the straight section of the angular tube; and
connected movably with the angular tube by at least one of a threaded connection and a sliding block guide and the mechanism and the ring can be detachably fixed in the different switching positions via at least one of the threaded connection, the sliding block guide and the mechanism.

13. A mask system comprising:
a respiration mask; and
an elbow, the elbow comprising:
an angular tube defining a breathing gas duct;
a tube port with an inlet opening for connecting to a breathing tube or Y-piece;
a mask port with an outlet opening for connecting to a respiration mask;
an anti-suffocation valve with an anti-suffocation opening, the anti-suffocation valve automatically and selectively providing a flow path from the mask port through the anti-suffocation opening to ambient air in case of a defect, said anti-suffocation valve being selectively able to be activated to provide the automatic and selective providing of said flow path, said anti-suffocation valve being selectively able to be deactivated to always block said flow path of said anti-suffocation valve;
carbon dioxide expiration opening arrangement, the carbon dioxide expiration opening arrangement being separate from the anti-suffocation valve and said anti-suffocation opening; and
a single switching member selectively movable for activating and deactivating of each of the anti-suffocation valve and one or more carbon dioxide expiration openings of the carbon dioxide expiration opening arrangement.

14. The mask system in accordance with claim 13, further comprising a first actuating element for activating and deactivating the anti-suffocation valve at the anti-suffocation valve and a second actuating element for activating and deactivating the carbon dioxide expiration openings at the carbon dioxide expiration openings, wherein one of:
the first actuating element and the second actuating element each comprise a mechanical functional connection mechanism with the switching member, the first actuating element and the second actuating element moving between an activation position and a deactivation position by means of the only one switching member; and
the elbow further comprises a mechanism for mechanically connecting the switching member to the first actuating element and to the second actuating element.

15. The mask system in accordance with claim 13, further comprising a first actuating element for activating and deactivating the anti-suffocation valve at the anti-suffocation valve and a second actuating element for activating and deactivating the carbon dioxide expiration openings at the carbon dioxide expiration openings, wherein at least one of:
the second actuating element is formed as a part of the switching member; and
the second actuating element is formed by a flap, a roller blind or a diaphragm.

16. The mask system in accordance with claim 13, wherein
the switching member is mounted movably between at least three different switching positions;
the anti-suffocation valve and the carbon dioxide expiration openings are activated in a first switching position of the at least three different switching positions of the switching member;
the anti-suffocation valve is activated and the carbon dioxide expiration openings are deactivated in a second switching position of the at least three different switching positions of the switching member; and
the anti-suffocation valve is deactivated and the carbon dioxide expiration openings are deactivated in a third switching position of the switching member.

17. The respiration valve arrangement in accordance with claim 1, wherein
the switching member is mounted movably between at least three different switching positions;
the anti-suffocation valve and the carbon dioxide expiration opening is activated to provide the flow path and to open the carbon dioxide expiration opening in a first switching position of the at least three different switching positions of the switching member;
the anti-suffocation valve opening is activated to provide the flow path and the carbon dioxide expiration opening is deactivated to close the carbon dioxide expiration opening in a second switching position of the at least three different switching positions of the switching member; and
the anti-suffocation valve is deactivated to close the flow path and the carbon dioxide expiration opening is deactivated to close the carbon dioxide expiration opening in a third switching position of the switching member.

18. A respiration valve arrangement comprising:
a tube port with an inlet opening adapted to connect to a breathing tube;
a mask port with an outlet opening adapted to connect to a respiration mask;
a middle section arranged between said tube port and said mask port;
an anti-suffocation valve arrangement in said middle section, said anti-suffocation valve arrangement automatically providing a flow path from said mask port through an anti-suffocation opening to ambient air if a defect;
a carbon dioxide expiration opening arranged in said middle section and being separate and spaced from said anti-suffocation opening;
a single switching member selectively movable into a plurality of positions by an operator, a first position of said plurality of positions closing said anti-suffocation opening and closing said carbon dioxide expiration opening independent of a defect, a second position of said switching member closing said carbon dioxide expiration opening and allowing said anti-suffocation valve arrangement to automatically provide said a flow path to ambient air if a defect, a third position of said switching member opening said carbon dioxide expiration opening and allowing said anti-suffocation valve arrangement to automatically provide said a flow path to ambient air if a defect.

19. The respiration valve arrangement in accordance with claim 18, further comprising a first actuating element activating said anti-suffocation valve arrangement to provide said flow path if a defect occurs and said first actuating element deactivating the anti-suffocation valve arrangement to close said anti-suffocation valve opening independent of a defect, and a second actuating element for activating and deactivating the carbon dioxide expiration opening at the carbon dioxide expiration opening, wherein one of:

the first actuating element and the second actuating element each comprise a mechanical functional connection mechanism with the single switching member, the first actuating element and the second actuating element moving between an activation position and a deactivation position by means of the single switching member; and the respiration valve arrangement further comprises a mechanism for mechanically connecting the switching member to the first actuating element and to the second actuating element.

20. The respiration valve arrangement in accordance with claim 18, further comprising a first actuating element activating said anti-suffocation valve arrangement to provide said flow path if a defect occurs, and said first actuating element deactivating the anti-suffocation valve arrangement to close said anti-suffocation valve opening independent of a defect, and a second actuating element for activating and deactivating the carbon dioxide expiration opening at the carbon dioxide expiration opening, wherein at least one of:

the second actuating element is formed as a part of the switching member; and the second actuating element is formed by a flap, a roller blind or a diaphragm.

* * * * *